(12) United States Patent
Gobber et al.

(10) Patent No.: US 9,907,875 B2
(45) Date of Patent: Mar. 6, 2018

(54) WICK FOR VOLATILE SUBSTANCE EVAPORATORS

(71) Applicant: ZOBELE ESPAÑA, S.A., Barcelona (ES)

(72) Inventors: Cedric Gobber, Barcelona (ES); Fernando Mayor Sans, Barcelona (ES); Jordi Masó Sabaté, Barcelona (ES)

(73) Assignee: ZOBELE ESPANA, S.A., Barcelona (ES)

( * ) Notice: Subject to any disclaimer, the term of this patent is extended or adjusted under 35 U.S.C. 154(b) by 0 days.

(21) Appl. No.: 15/325,658

(22) PCT Filed: Jul. 10, 2015

(86) PCT No.: PCT/ES2015/070541
§ 371 (c)(1),
(2) Date: Jan. 11, 2017

(87) PCT Pub. No.: WO2016/005646
PCT Pub. Date: Jan. 14, 2016

(65) Prior Publication Data
US 2017/0151361 A1   Jun. 1, 2017

(30) Foreign Application Priority Data

Jul. 11, 2014  (ES) ................................. 201431051

(51) Int. Cl.
*A61L 9/04*   (2006.01)

(52) U.S. Cl.
CPC ............. *A61L 9/04* (2013.01); *A61L 2209/13* (2013.01)

(58) Field of Classification Search
CPC .......................................................... A61L 9/04
USPC .......................................................... 502/404
See application file for complete search history.

(56) References Cited

U.S. PATENT DOCUMENTS 5,259,555 A    11/1993   Kiefer

FOREIGN PATENT DOCUMENTS

| | | |
|---|---|---|
| EP | 2594627 A1 | 5/2013 |
| WO | 2007098627 A2 | 9/2007 |
| WO | 2011121360 A1 | 10/2011 |

OTHER PUBLICATIONS

International Search Report from PCT/ES2015/070541, with an international filing date of Jul. 10, 2015, dated Sep. 2, 2015, 4 pgs., Spanish Patent Office, Madrid, Spain.

*Primary Examiner* — Edward Johnson
(74) *Attorney, Agent, or Firm* — Baker & Hostetler LLP

(57) ABSTRACT

The present invention relates to a wick for volatile substance evaporators formed from a strip (1) of wood and characterized in that the strip (1) has a height comprised between 120 mm and 170 mm, a width between 40 and 80 mm, in the widest part thereof, and a thickness between 1.5 mm and 3 mm. A more constant rate of evaporation of a fragrance or insecticide and a more balanced diffusion of fragrance or insecticide together with a greater intensity of the fragrance or of the insecticide efficacy in the room to be freshened or protected are achieved.

5 Claims, 3 Drawing Sheets

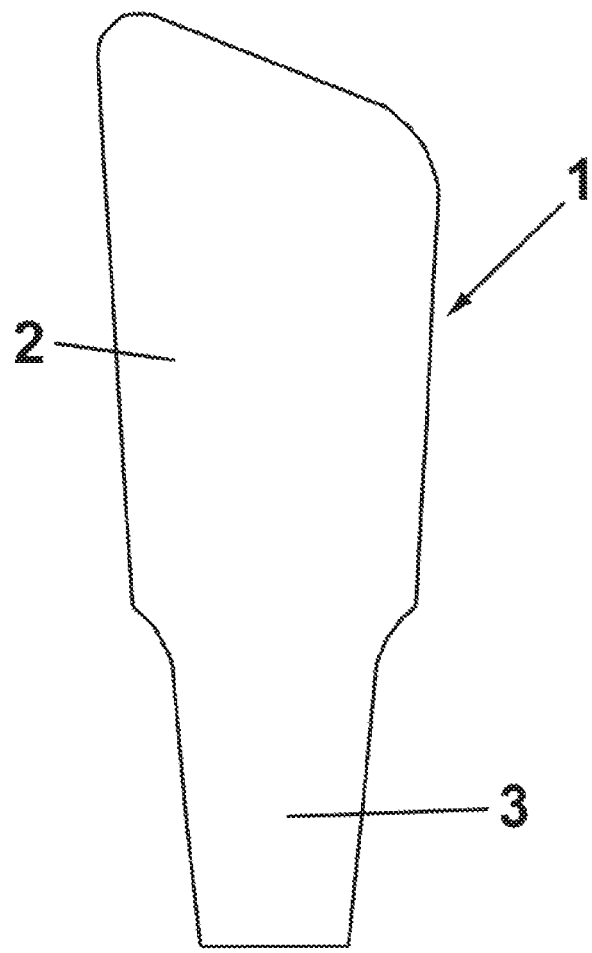

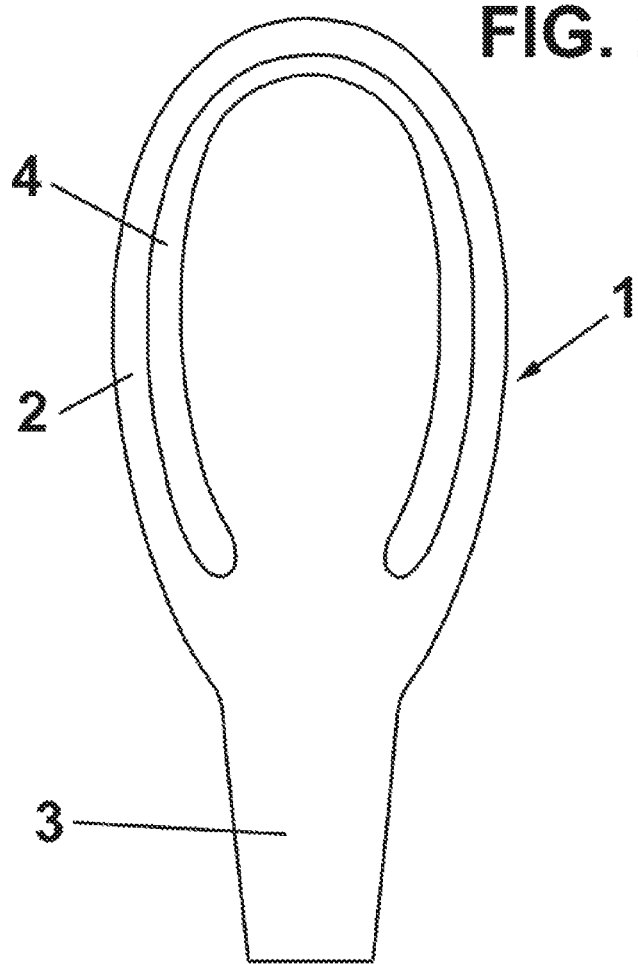

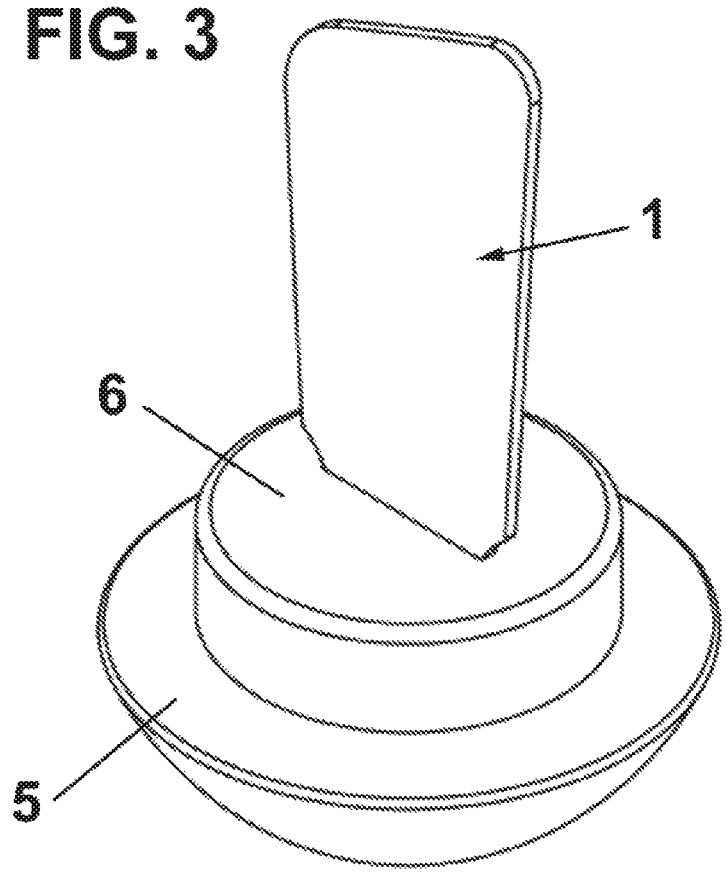

WICK FOR VOLATILE SUBSTANCE EVAPORATORS

CROSS-REFERENCE TO RELATED APPLICATIONS

This application is a U.S. National Stage filing, under 35 U.S.C. 371, of International Application No. PCT/ES2015/070541, filed Jul. 10, 2015, which claims the benefit of Spanish Application Serial No. P201431051, filed Jul. 11, 2014, the disclosures of which, including the specification, drawings, and abstract, are incorporated herein by reference in their entirety.

TECHNICAL FIELD OF THE INVENTION

The present invention relates to a wick for volatile substance evaporators for evaporating volatile substances, such as fragrances or insecticides, which is formed from a strip of wood.

BACKGROUND OF THE INVENTION

The use of wicks in volatile substance evaporators is known. These wicks are in contact with a liquid contained in a container, this liquid providing the volatile substances to be evaporated.

The wick soaks up these volatile substances by capillarity and they are evaporated into the surrounding area since the wick is in contact with the air.

The use of wood for making wicks is well known on the market. All these wicks work by adsorbing the fragrance through the wooden wick. Fragrance or insecticide evaporation occurs through the wick which is exposed to the environment.

The main drawback of these wooden wicks is their low rate of evaporation of volatile substances, so the diffusion thereof into the space to be freshened is reduced, the evaporation being neither constant nor balanced. This phenomenon negatively impacts the user's perception of the intensity of the evaporated fragrance.

There is therefore an obvious need for a wick in which the evaporation of volatile substances is constant over time.

DESCRIPTION OF THE INVENTION

The wick of the invention solves the mentioned drawbacks, having other advantages that will be described below.

The wick for volatile substance evaporators according to the present invention is formed from a strip of wood and is characterized in that the strip has a height comprised between 120 mm and 170 mm, a width between 40 and 80 mm, in the widest part thereof, and a thickness between 1.5 mm and 3 mm.

For example, the strip can have a height comprised between 140 mm and 150 mm, a width between 55 and 65 mm, in the widest part thereof, and a thickness between 2 mm and 2.5 mm.

Advantageously, said strip comprises a plurality of stratified grains, and as verified in practice, said strip is preferably a strip of birch wood, since it meets the grain stratification characteristics for achieving a constant evaporation.

Said strip preferably defines an upper area and a lower area in the normal position of use thereof, said upper area being wider than said lower area, such that said lower area can be housed inside a container with liquid for soaking the strip with the volatile substances to be evaporated.

As a result of the dimensions of the strip, a more constant rate of evaporation of a fragrance or insecticide and a more balanced diffusion of fragrance or insecticide together with a greater intensity of the fragrance or of the insecticide efficacy in the room to be freshened or protected are achieved.

BRIEF DESCRIPTION OF DRAWINGS

To better understand what has been set forth, drawings schematically depicting a practical embodiment only by way of a non-limiting example are attached.

FIG. 1 is a plan view of the wick according to the present invention, according to a possible first embodiment;

FIG. 2 is a plan view of the wick according to the present invention, according to a possible second embodiment; and FIG. 3 is a perspective view of the wick according to the present invention inserted in a stopper, which is in turn placed in a container.

DESCRIPTION OF A PREFERRED EMBODIMENT

The wick of the present invention is formed by the strip 1 made of wood, for example, birch wood with specific dimensions calculated to achieve a constant rate of evaporation of fragrance or insecticide over time.

The function of the birch wood wick is to move a fragrance or insecticide contained in a container through the strip by capillarity and diffuse it into the environment. Birch wood is particularly ideal for this function due to its genuine grain stratification.

Birch wood grains are natural capillaries and allow moving the fragrance or insecticide preferably through these capillaries, soaking the entire surface of the wick in a short period of time, and along with this characteristic there is a need to mention that birch wood has a large porosity which maximizes the user's perception of fragrance or insecticide efficacy.

These special characteristics of birch wood provide a constant rate of evaporation of fragrance or insecticide over time. A more balanced diffusion of the fragrance and a greater intensity of fragrance or insecticide efficacy in the room to be freshened or protected are thereby achieved.

To be able to attain the characteristics relating to fragrance evaporation and diffusion mentioned above, it is important to design the wick within specific dimensions.

The range of dimensions in which the wick will have these characteristics is as follows:

- height: 120 to 170 mm
- width: 40 to 80 mm, in the widest part thereof
- thickness: 1.5 to 3 mm
- wick evaporation surface: 6,000 to 10,000 mm2, on both sides.

It must be indicated that the strip 1 forming the wick according to the present invention can have any suitable regular or irregular shape provided that it is within the dimensions indicated above to achieve proper evaporation.

Said strip 1 preferably comprises an upper area 2 and a lower area 3 in the normal position of use thereof, the upper area 2 being wider than the lower area 3, as can be seen in the drawings.

According to the depicted embodiments, in FIG. 1 the upper edge of the strip 1 is inclined with respect to the longitudinal axis of the strip, whereas in FIG. 2 the strip comprises a curved groove 4.

For proper operation, the wick is mechanically inserted in a plastic stopper 6. This plastic stopper is inserted in a glass or plastic container 5 which contains volatile substances, such as a fragrance or insecticide, and is closed in a leak-tight manner before the first use.

Though not depicted in the drawings, the container 5 comprises a pressure compensation system therein formed by a hole covered completely by a porous membrane. This membrane allows the entry of air, but not the exit of liquid, causing the container to be leak-tight.

Before inserting the wick in the vessel, it is closed using an aluminum sealing film. This aluminum film closes the stopper 6 in which the wick is inserted in a leak-tight manner.

As a non-depicted alternative solution, leak-tightness can be achieved by means of applying a plastic plug closing the container.

Although reference has been made to a specific embodiment of the invention, it is obvious for a person skilled in the art that the wick for volatile substance evaporators described is susceptible to a number of variations and modifications, and that all the mentioned details can be replaced with other technically equivalent details without departing from the scope of protection defined by the attached claims.

The invention claimed is:

1. A wick for volatile substance evaporators formed from a strip (1) of wood, wherein the strip has a height comprised between 120 mm and 170 mm, a width between 40 and 80 mm, in the widest part thereof, and a thickness between 1.5 mm and 3 mm.

2. A wick for volatile substance evaporators according to claim 1, wherein the strip has a height comprised between 140 mm and 150 mm, a width between 55 and 65 mm, in the widest part thereof, and a thickness between 2 mm and 2.5 mm.

3. A wick for volatile substance evaporators according to claim 1, wherein said strip comprises a plurality of stratified grains.

4. A wick for volatile substance evaporators according to claim 1, wherein said strip is a strip of birch wood.

5. A wick for volatile substance evaporators according to claim 1, wherein said strip defines an upper area and a lower area in the normal position of use thereof, said upper area being wider than said lower area.

* * * * *